(12) United States Patent
Loisel

(10) Patent No.: US 10,631,946 B2
(45) Date of Patent: Apr. 28, 2020

(54) SYSTEM FOR ENDOSCOPIC INTRACRANIAL PROCEDURES

(71) Applicant: Penumbra, Inc., Alameda, CA (US)

(72) Inventor: Steven Loisel, Castro Valley, CA (US)

(73) Assignee: Penumbra, Inc., Alameda, CA (US)

( * ) Notice: Subject to any disclaimer, the term of this patent is extended or adjusted under 35 U.S.C. 154(b) by 325 days.

(21) Appl. No.: 15/360,241

(22) Filed: Nov. 23, 2016

(65) Prior Publication Data

US 2017/0151032 A1 Jun. 1, 2017

Related U.S. Application Data

(60) Provisional application No. 62/261,147, filed on Nov. 30, 2015.

(51) Int. Cl.
| | | |
|---|---|---|
| *A61B 90/10* | (2016.01) | |
| *A61B 34/20* | (2016.01) | |
| *A61B 90/11* | (2016.01) | |
| *A61B 90/00* | (2016.01) | |
| *A61B 17/34* | (2006.01) | |
| *A61B 17/22* | (2006.01) | |

(52) U.S. Cl.
CPC .............. *A61B 90/10* (2016.02); *A61B 34/20* (2016.02); *A61B 90/11* (2016.02); *A61B 2017/22014* (2013.01); *A61B 2017/3407* (2013.01); *A61B 2017/347* (2013.01); *A61B 2090/061* (2016.02); *A61B 2090/062* (2016.02); *A61B 2090/103* (2016.02); *A61B 2090/3937* (2016.02); *A61B 2217/005* (2013.01); *A61B 2217/007* (2013.01)

(58) Field of Classification Search
CPC .............. A61B 90/11; A61B 2090/103; A61B 2017/3407; A61M 2039/025
See application file for complete search history.

(56) References Cited

U.S. PATENT DOCUMENTS

| | | | |
|---|---|---|---|
| 4,809,694 A | | 3/1989 | Ferrara |
| 6,609,020 B2 | | 8/2003 | Gill |
| 7,204,840 B2 | | 4/2007 | Skakoon et al. |
| 7,559,935 B2 | | 7/2009 | Solar et al. |
| 7,604,644 B2 | | 10/2009 | Schulte et al. |
| 7,660,621 B2 | | 2/2010 | Skakoon et al. |
| 7,695,480 B2 | | 4/2010 | Solar et al. |
| 7,988,674 B2 | | 8/2011 | Adams et al. |
| 8,679,088 B2 | | 3/2014 | Abrahams |
| 8,747,419 B2 | | 6/2014 | Solar et al. |
| 8,845,656 B2 | | 9/2014 | Skakoon et al. |
| 2002/0049451 A1 | * | 4/2002 | Parmer .................. A61B 90/11 606/108 |

(Continued)

FOREIGN PATENT DOCUMENTS

| | | | |
|---|---|---|---|
| CA | 2240456 | * | 4/1998 |
| EP | 1549241 B1 | | 5/2010 |

*Primary Examiner* — Thomas McEvoy
(74) *Attorney, Agent, or Firm* — Wilson Sonsini Goodrich & Rosati

(57) ABSTRACT

A system for intracranial access that includes a support assembly is described. The support assembly has a hub and lobes surrounding a central aperture for introducing a sheathed core that can accommodate an endoscope and/or other devices. Some embodiments include a collar and a ring, each of which can be tightened to secure the sheathed core in place. An accessory device for use during intracranial aspiration procedures is described.

36 Claims, 17 Drawing Sheets

(56) References Cited

U.S. PATENT DOCUMENTS

2004/0167542 A1\* 8/2004 Solar ..................... A61B 90/11
                                                    606/130
2007/0038100 A1   2/2007 Nita
2014/0148654 A1   5/2014 Abrahams
2015/0057570 A1\* 2/2015 Chin ................. A61B 10/0283
                                                    600/566

\* cited by examiner

SYSTEM FOR ENDOSCOPIC INTRACRANIAL PROCEDURES

CROSS-REFERENCE TO RELATED APPLICATIONS

This application claims the benefit of the priority date of U.S. Provisional Application No. 62/261,147, filed Nov. 30, 2015, the entire content of which is incorporated herein by reference.

FIELD OF THE INVENTION

The present invention relates generally to the field of medical devices and methods. More specifically, the invention described herein relates to devices and methods that support endoscopic medical procedures involving access to the interior of the skull, and that aid in the safe manipulation of devices during procedures requiring access to the interior of the skull.

BACKGROUND OF THE INVENTION

Numerous medical procedures require intracranial entry through the skull to treat tissue in the interior of the skull. Examples of such endoscopic procedures include endoscopic tumor biopsy, tumor evacuation, stroke treatment, treatment of intracranial cysts, hydrocephalus therapy, and others. All such procedures require a safe apparatus and method for accessing the interior of the skull. Many of the procedures also require removal and reentry of devices into the operative field. And all such procedures require safe handling of the apparatus and devices throughout the procedure.

Among the foregoing examples of medical conditions, stroke is a significant cause of disability and death, and a growing problem for global healthcare. More than 700,000 people in the United States alone suffer a stroke each year, and of these, more than 150,000 people die. Of those who survive a stroke, roughly 90% will suffer long term impairment of movement, sensation, memory, or reasoning, ranging from mild to severe. The total cost to the U.S. healthcare system is estimated to be over $50 billion per year.

Stroke may be caused from a blockage in a cerebral artery resulting from a thromboembolism (referred to as an "ischemic stroke"), or by a rupture of a cerebral artery (referred to as a "hemorrhagic stroke"). A thromboembolism is a detached blood clot that travels through the bloodstream and lodges in a manner that obstructs or occludes a blood vessel. Roughly 80% of strokes classified as ischemic, with the remaining 20% classified as hemorrhagic.

Hemorrhagic stroke results in bleeding within the skull, limiting blood supply to brain cells, and placing harmful pressure on delicate brain tissue. Blood loss, swelling, herniation of brain tissue, and pooling of blood that results in formation of clot mass inside the skull all rapidly destroy brain tissue. Hemorrhagic stroke is a life threatening medical emergency, for which improvements in treatment are evolving. An example of treatment of stroke includes the therapeutic administration of high frequency, low intensity ultrasound, referred to as trans-cranial Doppler (TCD). An exemplary procedure involves creation of a bur hole in the skull, and introduction of a wand that can deliver ultrasound therapy. The ultrasound therapy disrupts and removes clots, thereby immediately reducing the dangerous pressure exerted on vital brain tissue. Combined with visualization and aspiration, the therapy has been shown to safely treat hemorrhagic stroke. Other cerebral disorders may also benefit from the administration of high-frequency, low intensity ultrasound, or TCD. Examples include dementia, head trauma, intracranial hematoma, Alzheimer's, and other abnormalities.

In order to safely administer TCD, the surgeon and other clinicians must introduce the ultrasound wand and/or aspiration wand through a burr hole and into the skull. The wand must be safely manipulated throughout the procedure. Among other safety concerns, the surgeon must be aware of the depth of penetration of the wand into the skull. In addition, it is desirable to visualize the lateral and medial orientation of the wand within the skull. Visualization of surrounding structures may be difficult due to the limited space of the burr hole. Additionally, because many pieces of equipment, both large and small, are involved in the procedure, a clinician may be required to leave an endoscope in place in order to made adjustments to or otherwise manipulate other devices, and to remove devices and reenter the operative field with an alternative device. Therefore, it is desirable to improve the apparatus and method by which the wand is introduced through the skull, the method by which reentry is achieved, and the apparatus and method by which the access device is stabilized throughout the procedure.

DETAILED DESCRIPTION OF THE INVENTION

Some embodiments of the invention are described below. For clarity, not all features of each actual implementation are described in this specification. In the development of an actual device, some modifications may be made that result in an embodiment that still falls within the scope of the invention.

Figure 1:
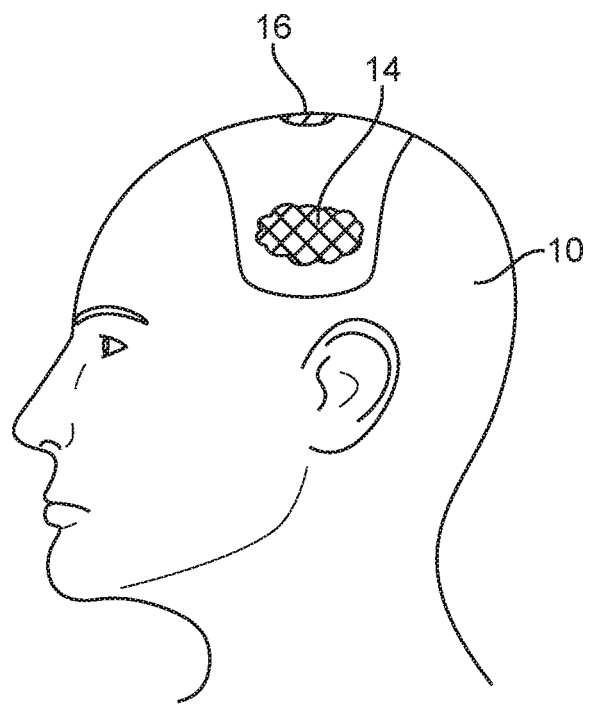
FIG. 1 is a partial see-through, schematic depiction of an early step in an endoscopic intracranial procedure.
Figure 2:
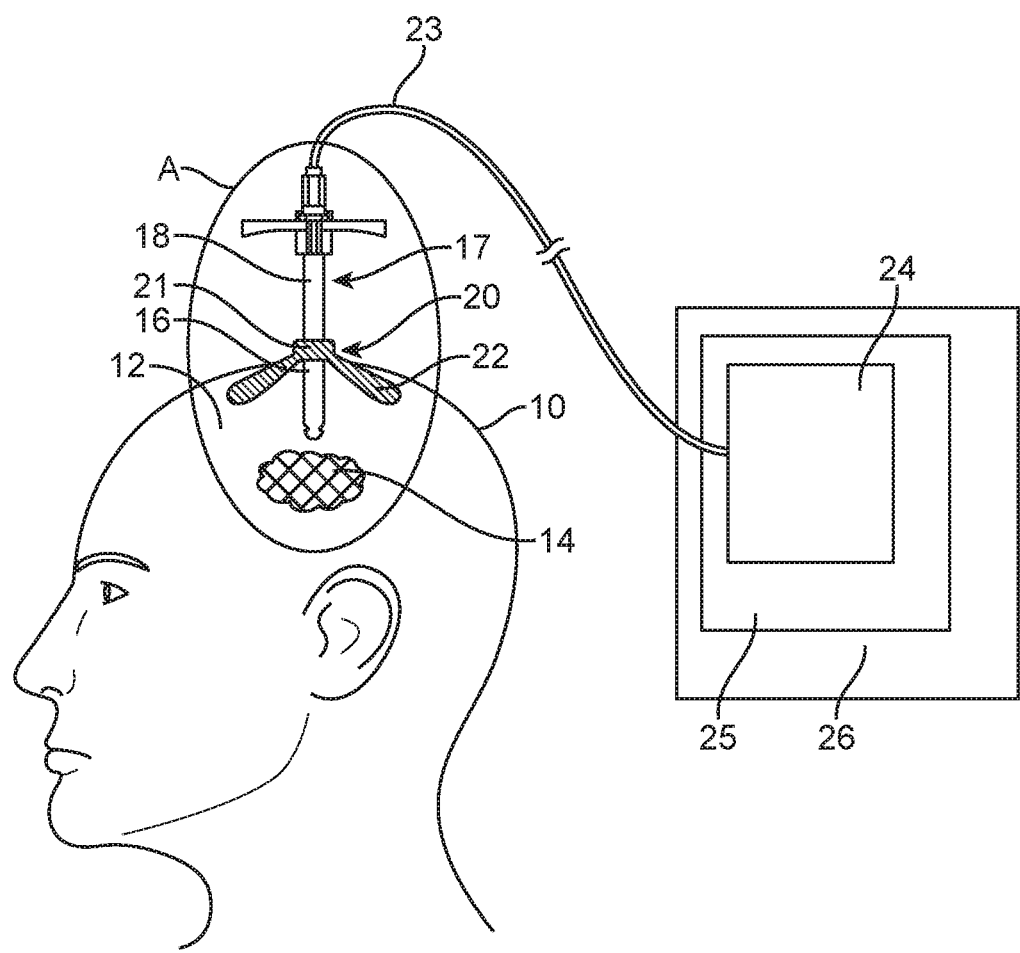
FIG. 2 is a partial see-through, schematic depiction of another early step in an endoscopic intracranial procedure.

FIG. 1 and FIG. 2 are schematic illustrations of an early phase of an endoscopic, intracranial procedure. The medical procedure depicted in simplified form in FIGS. 1 and 2 may be any of a number of procedures, including tumor biopsy, tumor evacuation, removal of intracranial hematoma, removal of excess fluid, or other endoscopic procedure. The procedure depicted may or may not include aspiration, administration of ultrasound therapy, and/or other techniques. A system according to the invention and illustrated here may have utility in a number of exemplary procedures. The procedure most likely will be performed utilizing fluoroscopic or other imaging techniques. In FIG. 1, patient's skull 10 is illustrated. Skull 10, shown as partially "see-through", has interior 12. Interior 12 is afflicted with a lesion or mass 14. In a previous step in the procedure, burr hole 16 was formed on patient's skull 10, providing access from the exterior of skull 10 to the interior 12. Burr hole 16 will permit access for treatment of mass 14.

As illustrated in FIG. 2, endoscopic system 17 is then utilized to carry out one or more procedures. Endoscopic system 17 includes wand 18, which may be introduced through burr hole 16 into interior 12 of skull 10. Wand 18 may be designed to carry out aspiration of fluid and tissue, to administer ultrasound therapy, and/or to perform other therapeutic functions. After introduction of wand 18 through burr hole 16, support accessory 20 is used to stabilize system 17. Support accessory 20, which is illustrated in greater detail in FIGS. 4 and 5, stabilizes system 17 via hub 21 and lobes 22. Lobes 22 may be sutured, stapled, or otherwise affixed to skull 10. In the example of FIG. 2, wand 18 is connected via tubing 23 to collection canister 24. Collection canister 24 may optionally be a component of a larger system that includes vacuum 25, ultrasound generator 26, and/or other components.

Figure 3:
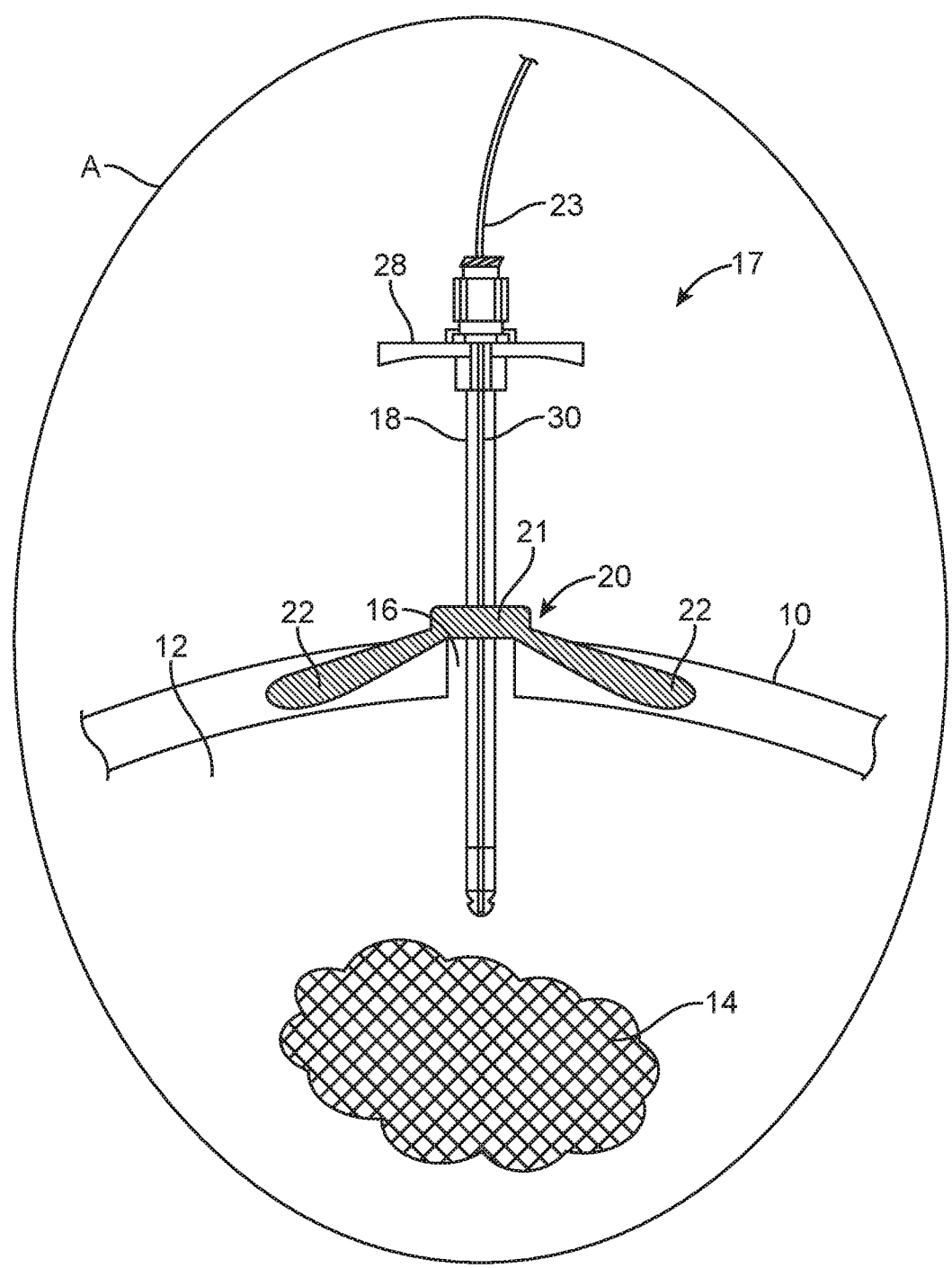
FIG. 3 is an enlargement of Area A of FIG. 2.

Turning now to FIG. 3, Area A of FIG. 2 is expanded to show detail. Endoscopic system 17 is illustrated, with wand 18 positioned through burr hole 16 of skull 10. Endoscopic system 17 can thereby access interior 12, and ultimately lesion or mass 14. Wand 18 extends from the exterior of skull 10, through burr hole 16, and into interior 12. Support accessory 20, described in greater detail below and illustrated in FIGS. 4 and 5 below, stabilizes wand 18 in position through burr hole 16. Wand 18 is slid through hub 21 via a hole or central aperture 42 (not visible in FIG. 3), and is press fit engaged with hub 21. That is, wand 18 can be pushed through the central aperture of hub 21, and retracted through the central aperture of hub 21, and otherwise vertically adjusted through hub 21 at the election of the physician. Hub 21 of support accessory 20 is attached to lobes 22 of support accessory 20. During a procedure, lobes 22 can be secured to skull 10 via sutures, staples, screws, adhesive, or other manner (not pictured in FIG. 3). While stabilized by support accessory 20 and secured to skull 10, endoscopic system 17 can then be readily employed in an intracranial endoscopic procedure such as in one of the examples set forth above. Grips 28 of endoscopic system 17 are visible in FIG. 3, as is score line 30, both of which will be described in greater detail below. Tubing 23, extending from system 17, is also visible in FIG. 3.

Figure 4:
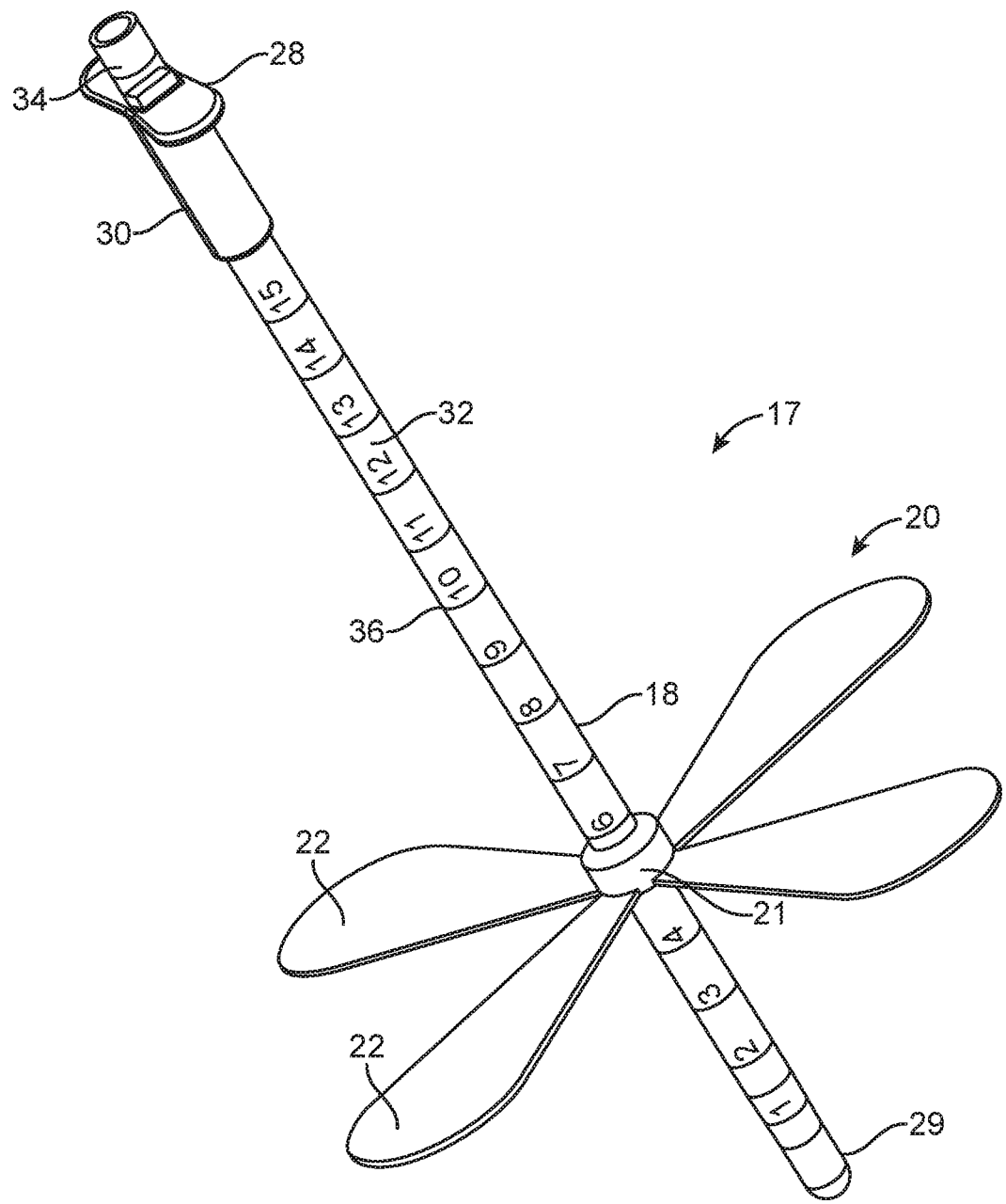
FIG. 4 is a perspective view of an embodiment according to the invention.

FIG. 4 is a perspective view of endoscopic system 17, shown in isolation, so that its details can be more readily viewed. Endoscopic system 17 includes two major components: wand 18 and support accessory 20. Wand 18, which terminates in atraumatic distal tip 29, is composed of two major components: outer sheath 32 and inner core 34. (Only the proximal most portion of inner core 34 is visible in FIG. 4.) Outer sheath 32 and inner core 34 are preferably fabricated from biocompatible polymers, either synthetic or natural, but most preferably clear polyamides. Outer sheath 32 and inner core 34 may be of any suitable length, but are most likely between 3 and 10 inches in length. Outer sheath 32 may be sized to any suitable diameter, but most often will be sized to accommodate between 18 French guide catheters (FR) and 22 FR. Inner core 34 is more visible in FIG. 5, and will be described in more detail below. Outer sheath 32 is marked with measured demarcations 36. Outer sheath 32 may also optionally include longitudinal lines on each side of outer sheath 32, in order to indicate lateral and medial orientation of wand 18.

Outer sheath 32 also includes grips 28, for gripping by the physician in order to manipulate endoscopic system 17. While held via grips 28, endoscopic system 17 can be introduced through a burr hole into the interior of a patient's skull (not pictured in FIG. 4). Utilizing demarcations 36, a physician can monitor and regulate the depth of wand 18 into the interior of the patient's skull. As described above in relation to FIG. 3, wand 18 is slidingly positionable through hub 21 of support accessory 20. In FIG. 4, wand 18 is positioned roughly between the $4^{th}$ and $6^{th}$ of demarcations 36, but wand 18 can be pushed, for example, to the $13^{th}$ or $14^{th}$ demarcations 36, or withdrawn, for example, to the $2^{nd}$ demarcation. Ultimately wand 18 can be completely withdrawn from hub 21 of support accessory 20. Support accessory 20 is preferably fabricated from a semi-rigid biocompatible polymer, but may be made from alternative suitable materials. Also visible in FIG. 4, though only slightly, is score line 30, between grips 28. Score line 30 in fact extends most or all of the length of wand 18, and is illustrated in greater detail in FIG. 6.

Figure 5:
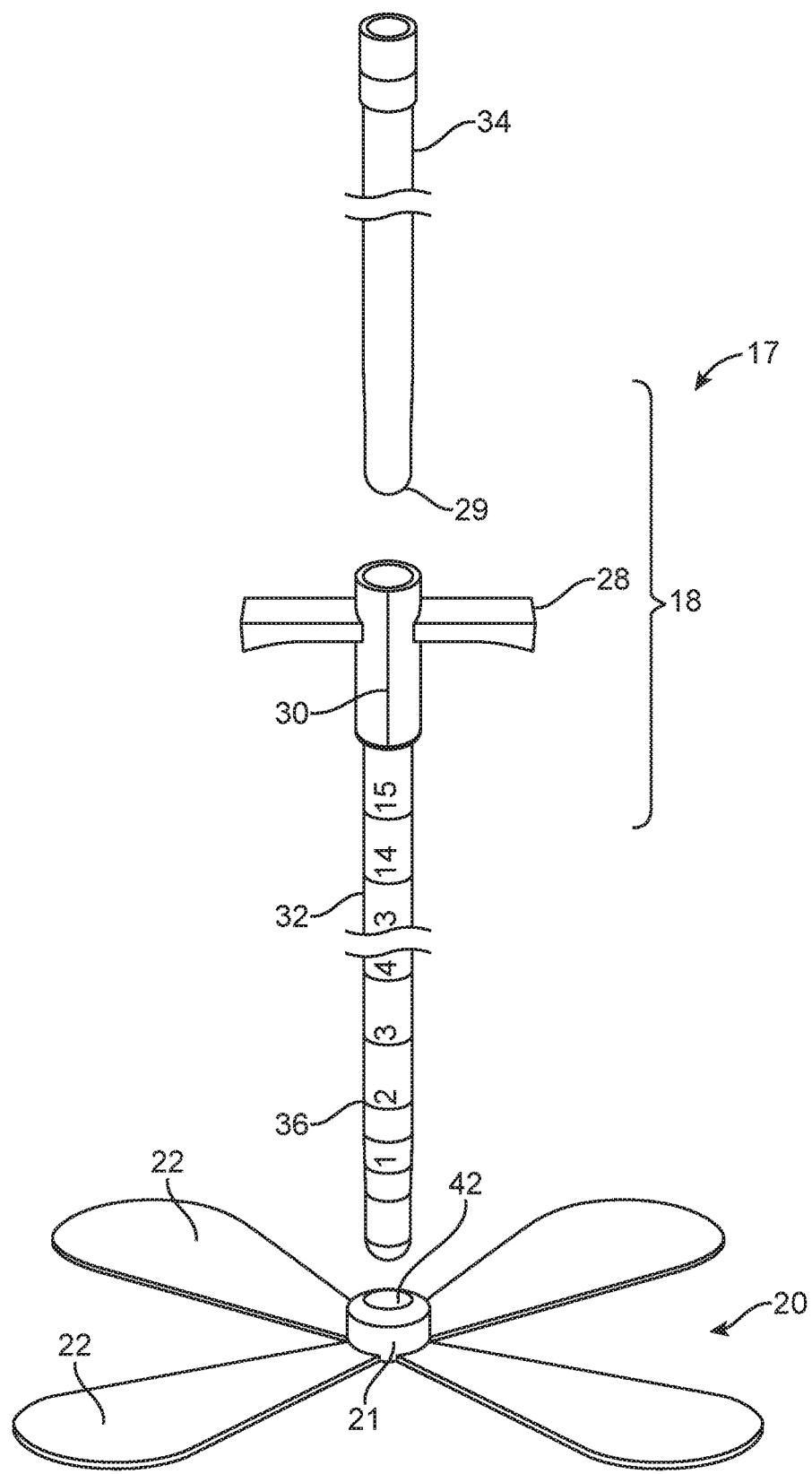
FIG. 5 is an exploded view of the embodiment of FIG. 4.

FIG. 5 is an exploded view of FIG. 4. In FIG. 5, the view of endoscopic system 17 is oriented so that score line 30 is visible. In addition, wand 18 is illustrated as withdrawn from hub 21, and inner core 34 is shown removed from outer sheath 32. When endoscopic system 17 is in use, inner core 34 extends through the interior of outer sheath 32, and wand 18 is threaded through hub 21 of support accessory 20. Inner core 34 may accommodate the introduction of a neuroendoscope, an aspiration catheter, an ultrasound therapy wand, or other device. Moreover, inner core 34 may safely accommodate reentry of devices into the surgical field. Inner core 34 alternatively may include one or more side ports (not pictured) in order to accommodate multiple entry points, or multiple devices. Measured demarcations 36 are visible on outer sheath 32, just as they are visible when endoscopic system 17 is assembled for use.

Figure 6:
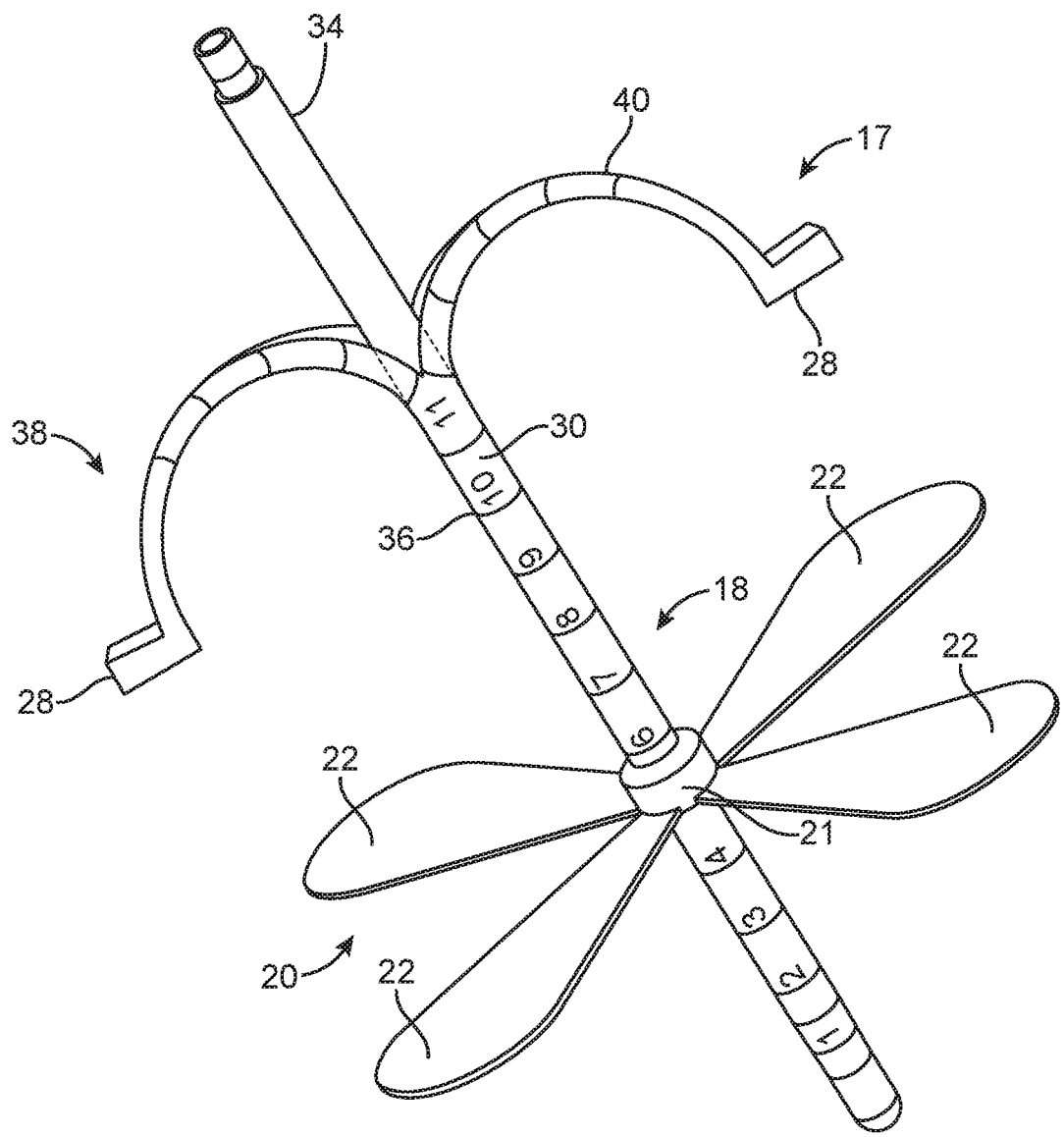
FIG. 6 is a perspective view of the embodiment of FIG. 4, with the peel-apart sheath shown pulled apart.

FIG. 6 illustrates endoscopic system 17 as assembled for use. In addition, FIG. 6 illustrates endoscopic system 17 as it would appear during a phase of a procedure subsequent to that illustrated in FIG. 4. Specifically, after endoscopic system 17 is introduced through a burr hole in the skull (not pictured in FIG. 6), lobes 22 may be secured to the exterior of the patient's skull as described above. Support accessory 20 will thereby stabilize the upright orientation of wand 18 while it is in use. Further, wand 18 may be vertically adjusted through hub 21, to penetrate into the intracranial space to a desired depth, as monitored using measured demarcations 36. The orientation of endoscopic system 17 may also be judged using longitudinal markers (not pictured) on outer sheath 32.

Following the positioning of endoscopic system 17 as described above, outer sheath 32 can then be pulled apart. Using grips 28, outer sheath can be pulled to separate along score line 30. Outer sheath 32 is thereby partially divided into separate halves 38 and 40. Separate halves 38 and 40 may then optionally be secured to lobes 22 or to the patient's skull (not pictured). Pulling apart outer sheath 32 exposes inner core 34, through which an endoscope, aspiration catheter, ultrasound wand, and/or other devices may be introduced and withdrawn. Wand 18 can be withdrawn, and endoscopic system 17 can be removed upon the conclusion of the procedure.

Figure 7:
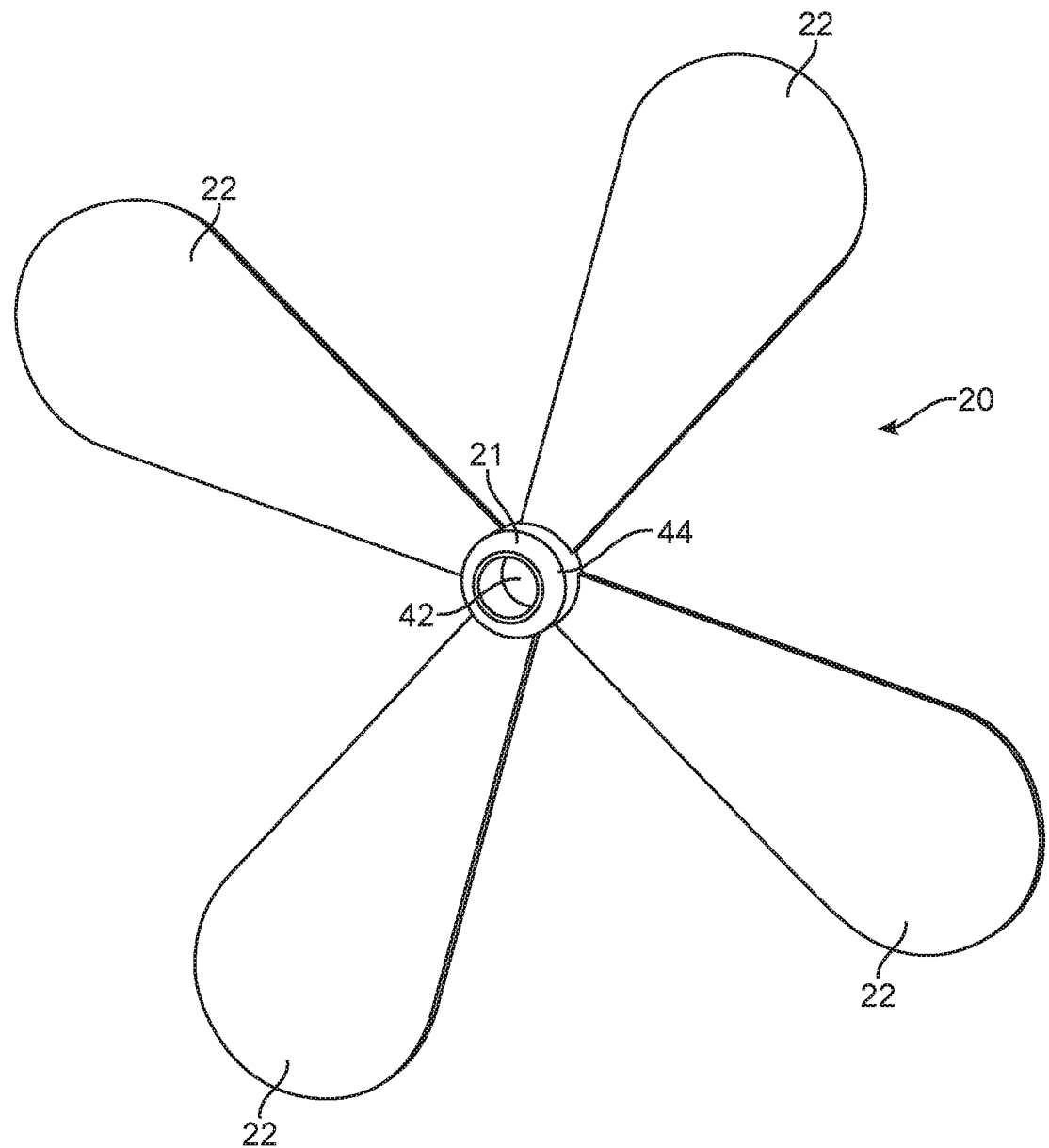
FIG. 7 is a perspective view of a component of the embodiment of FIG. 4.

FIG. 7 illustrates support accessory 20 by itself. Support accessory 20 includes hub 21, which surrounds a through hole, or central aperture 42. The inner diameter of through hole or central aperture 42 can range from 0.2 inch to 0.4 inch. A wand or other elongate device may be introduced via central aperture 42. Hub 21 has walls 44. Attached to hub 21, at the base of walls 44, are lobes 22. Support accessory 20 has four lobes, but any suitable number of lobes may be included. Lobes 22 are thin, flat, semi-rigid or rigid elements. Lobes 22 are relatively narrow at their site of attachment to hub 21, and broaden as they extend away from hub 21. Overall, support accessory 20 defines a flower-like or a fan-like structure, though alternative structures may be suitable according to the invention. Lobes 22 are relatively thin, being of suitable thickness for the passage of sutures or staples or comparable affixation devices. Alternatively, the underside of lobes 22 may be equipped with adhesive for securing support accessory 20 to a patient's head. Also alternatively, the top side of lobes 22 may be equipped with adhesive in order to secure elements (such as, for example halves of a pulled-apart sheath) to the top of lobes 22. Lobes 22 may be between 1 inches and 8 inches in length, and support accessory may be between 2.25 inches and 9 inches in diameter.

Figure 8:
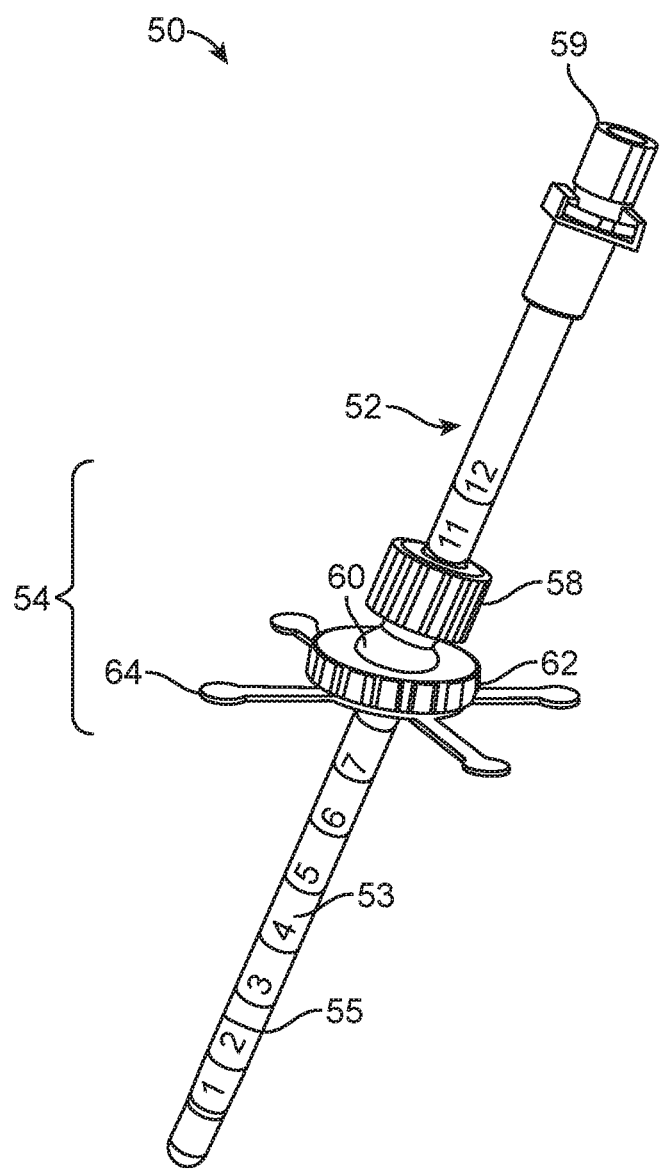
FIG. 8 is a perspective view of an alternative embodiment according to the invention.
Figure 11:
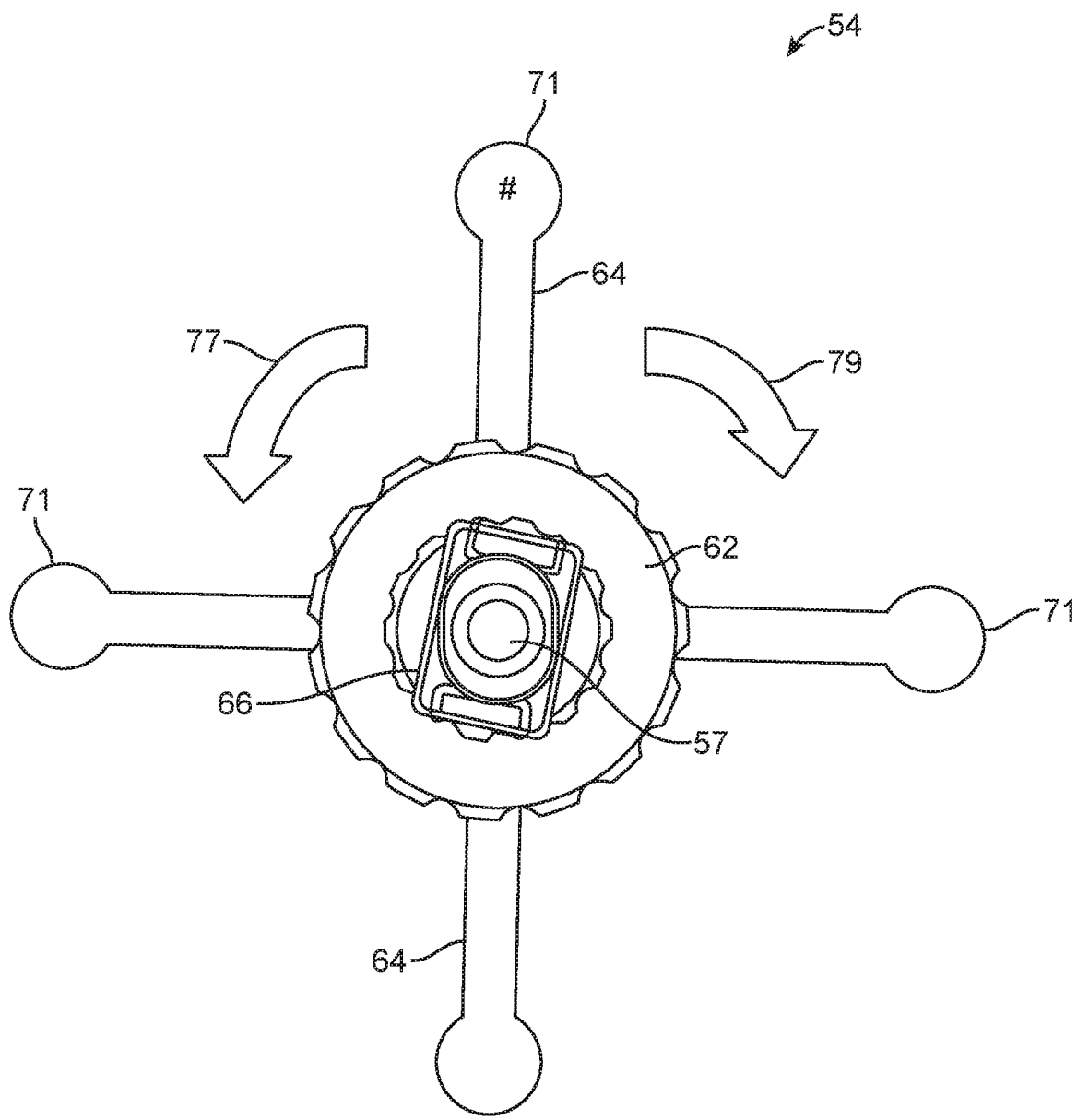
FIG. 11 is a bottom view of a component of the embodiment of FIG. 8.

FIG. 8 illustrates an alternative embodiment according to the invention, from a perspective view. The embodiment of FIG. 8 incorporates many of the general principles and features of the embodiments described above, but it also includes additional characteristics and capabilities. System 50 includes wand 52 and support assembly 54. Wand 52 is constructed in the same manner as wand 18 described above, and includes an outer sheath 53 disposed over an inner core 59. When system 50 is assembled for use, wand 52 is disposed through a central aperture 57 (visible in FIG. 11) of support assembly 54. Measured demarcations are visible on the exterior surface of outer sheath 53.

Figure 9:
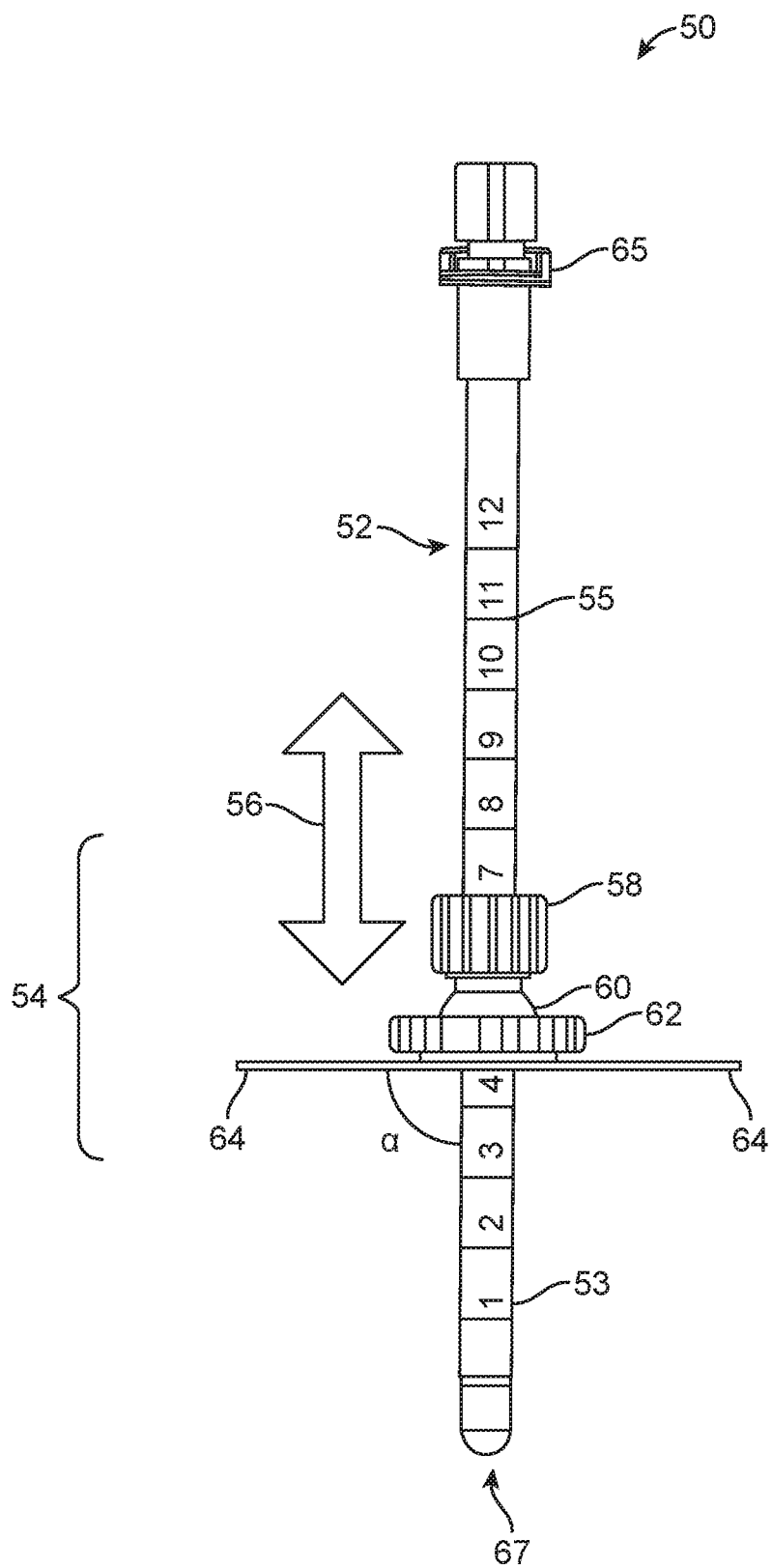
FIG. 9 is a side elevation view of the embodiment of FIG. 8.

The embodiment is illustrated in a side elevation view in FIG. 9. System 50 is shown as assembled for use. Wand 52 is introduced through the center of support assembly 54, and wand 52 is movable along most of its length in the directions of arrows 56, and is additionally rotatable about its axis, until it is locked in vertical position by collar 58, as described in greater detail below. Measured demarcations 55 indicate the depth of introduction of wand 52 through support assembly 54, and consequently, when in actual use, indicate the depth of penetration of wand 52 into a patient's skull. In FIG. 9, wand 52 is shown essentially vertical, and displays more or less a 90° vertical orientation angle α. Wand 52 however can be tilted, thereby changing the vertical orientation angle.

Figure 10:
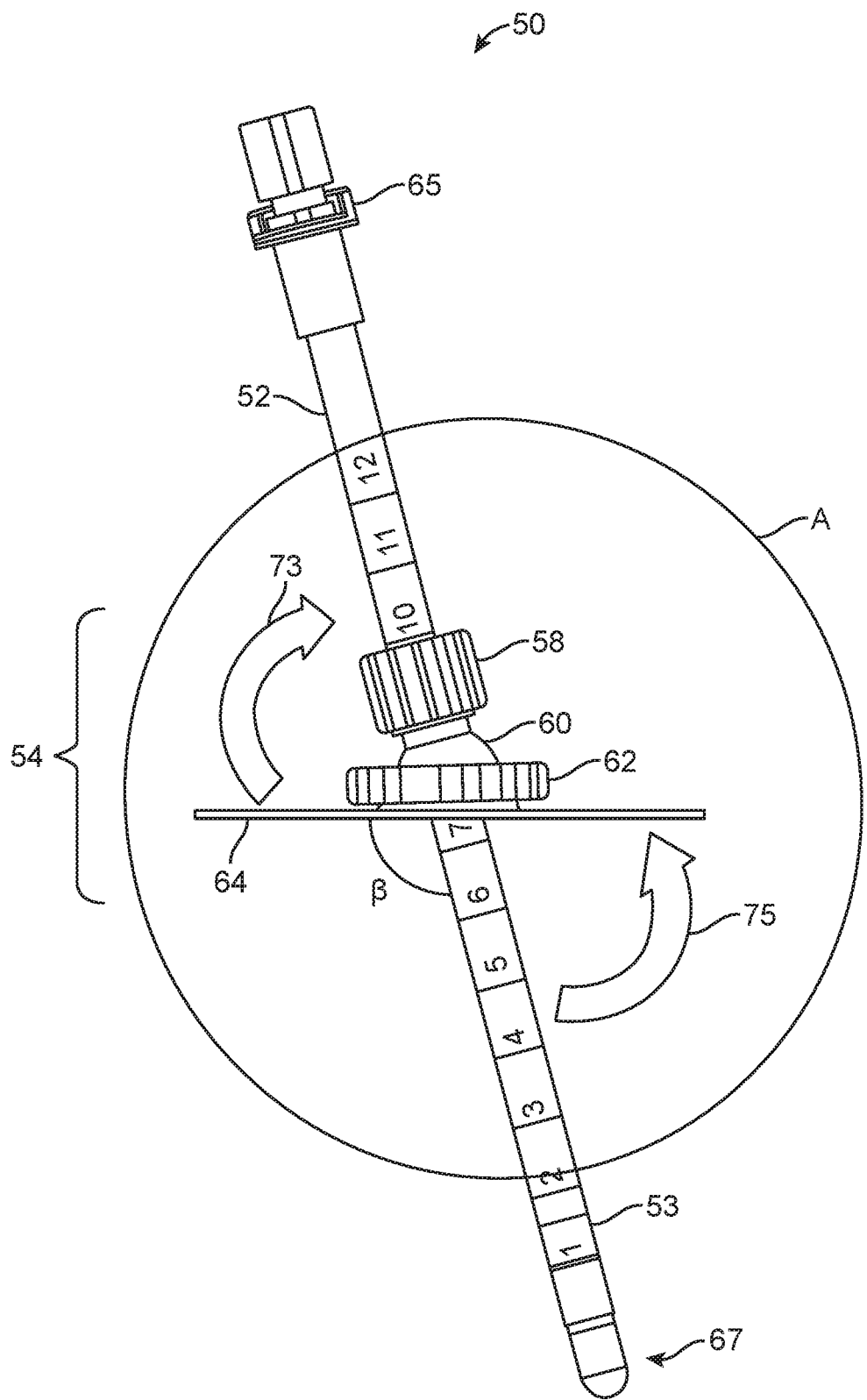
FIG. 10 is a side elevation view of the embodiment of FIG. 8, after an adjustment in position of the system.

As illustrated in FIG. 10, the angle of vertical orientation can be adjusted, or tilted. In FIG. 10, the vertical orientation angle has been adjusted to now define angle β. Wand 52 can be tilted essentially in all directions, and tilted back to the vertical position. Arrows 73 and 75 illustrate two directions in which wand 52 can be tilted. This feature is very advantageous for optimal positioning of wand 52 for access to a treatment site, and optimal positioning of all instruments and devices introduced through wand 52. Once the desired angular orientation of wand 52 is reached, wand 52 can be locked in the desired orientation by ring 62, as described in greater detail below. Returning for now to FIG. 10, support assembly 54 is made up of component pieces collar 58, tilting element 60, ring 62, lobes 64 (and hub 66, visible in FIG. 11 and FIG. 12). Collar 58, tilting element 60, ring 62, and hub 66 all include a central aperture through which wand 52 can be introduced. Collar 58 is secured to tilting element 60, and both collar 58 and tilting element 60 are slidingly secured to wand 52. Ring 62 is secured to hub 66, which is tiltably secured to tilting element 60. Tilting element 60 permits tilting adjustment of hub 66, which thereby causes tilting of lobes 64 about tilting bulb 60, and consequently permits adjustment of the vertical angle of wand 52. In actual use, support assembly 54 is secured to a patient's skull via lobes 64. Support assembly 54 therefore provides support to wand 52, while at the same time permitting some freedom of movement. This freedom of movement is very advantageous for manipulation of system 50 during use of system 50 in therapy, when targeting a mass, clot, or accumulation of blood. In use, a clinician grasps grasper 65 and inserts distal end 67 into a burr hole in the patient's skull (not pictured). Lobes 64, which have broadened regions 71, are affixed to the patient's skull via staples, sutures, adhesive, or other suitable means (not pictured). Wand 52 is moved to a desired depth through the burr hole, by moving wand along the directions of arrows 56. When the desired depth is reached, collar 58 is tightened, and wand 52 is lock into vertical position. Further, wand 52 is tilted in all directions about its vertical axis, including in the directions similar to that represented by arrows 73 and/or 75, of FIG. 10, until the desired position for access to the mass (such as mass 14 of FIG. 1) is achieved. Once the desired orientation is achieved, giving optimal access to mass 14, ring 62 is rotated until it is tightened, and the angular orientation is thereby locked into place. Support assembly 54 accordingly helps maintain the position of system 50, even if a clinician must withdraw his or her hand for a moment.

Figure 12:
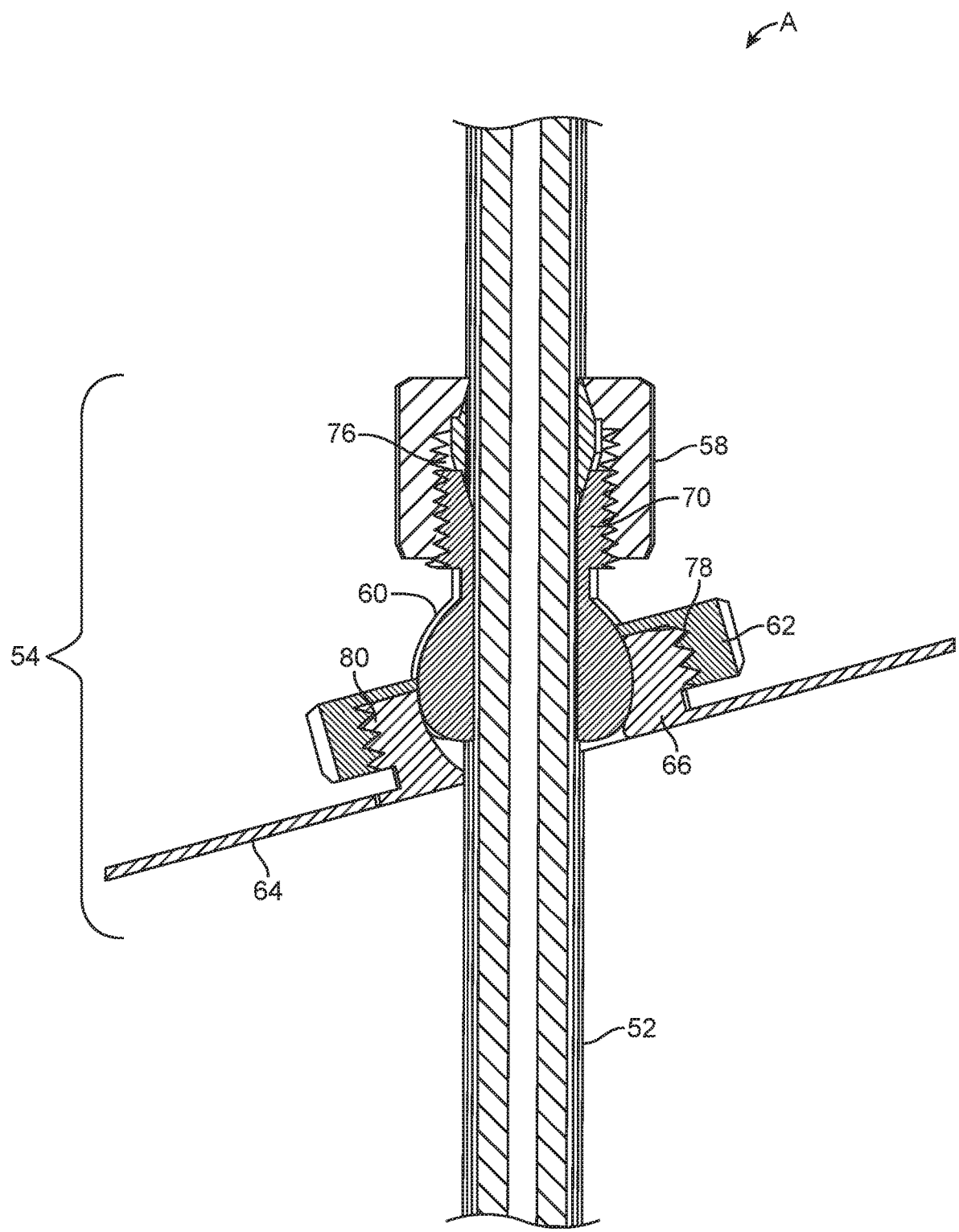
FIG. 12 is a detailed cross sectional side view of Area A of FIG. 10.
Figure 13:
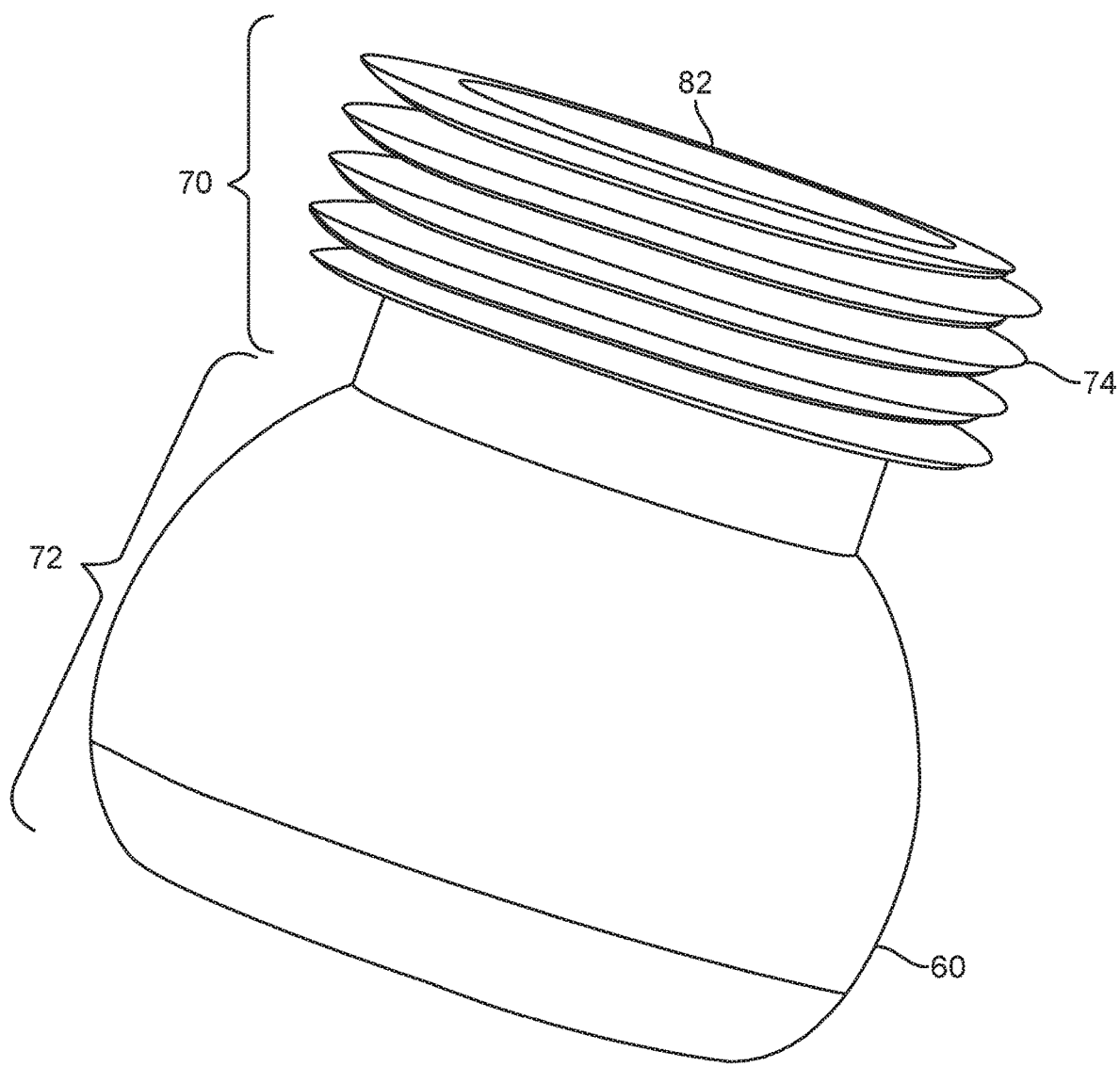
FIG. 13 is a perspective view of a component of the embodiment of FIG. 8.

As most easily viewed in FIG. 12, optional interlocking features 76 of collar 58 help collar 58 secure tilting element 60, and also secure support assembly 54 to wand 52. Illustrated separately in FIG. 13, tilting element 60 includes neck 70 and bulb 72. In the embodiment of FIG. 13, neck 70 includes screw threads 74. But other configurations, such as engagement ribs, male/female features or other surface features optimized for engaging, mating or securing an opposing surface are within the scope of the invention. Screw threads 74 mate with the optional complementary interlocking features 76. Collar 58 can be rotated clockwise to tighten engagement of interlocking features 76 and screw threads 74. Collar 58 can be rotated until collar 58 and neck 70 are tightly engaged to wand 52. When collar 58 is fully tightened, wand 52 is no longer movable in a vertical direction. Therefore, in use, when the desired depth of wand 52 is reached, collar 58 may be tightened to lock wand 52 in place vertically.

Figure 14:
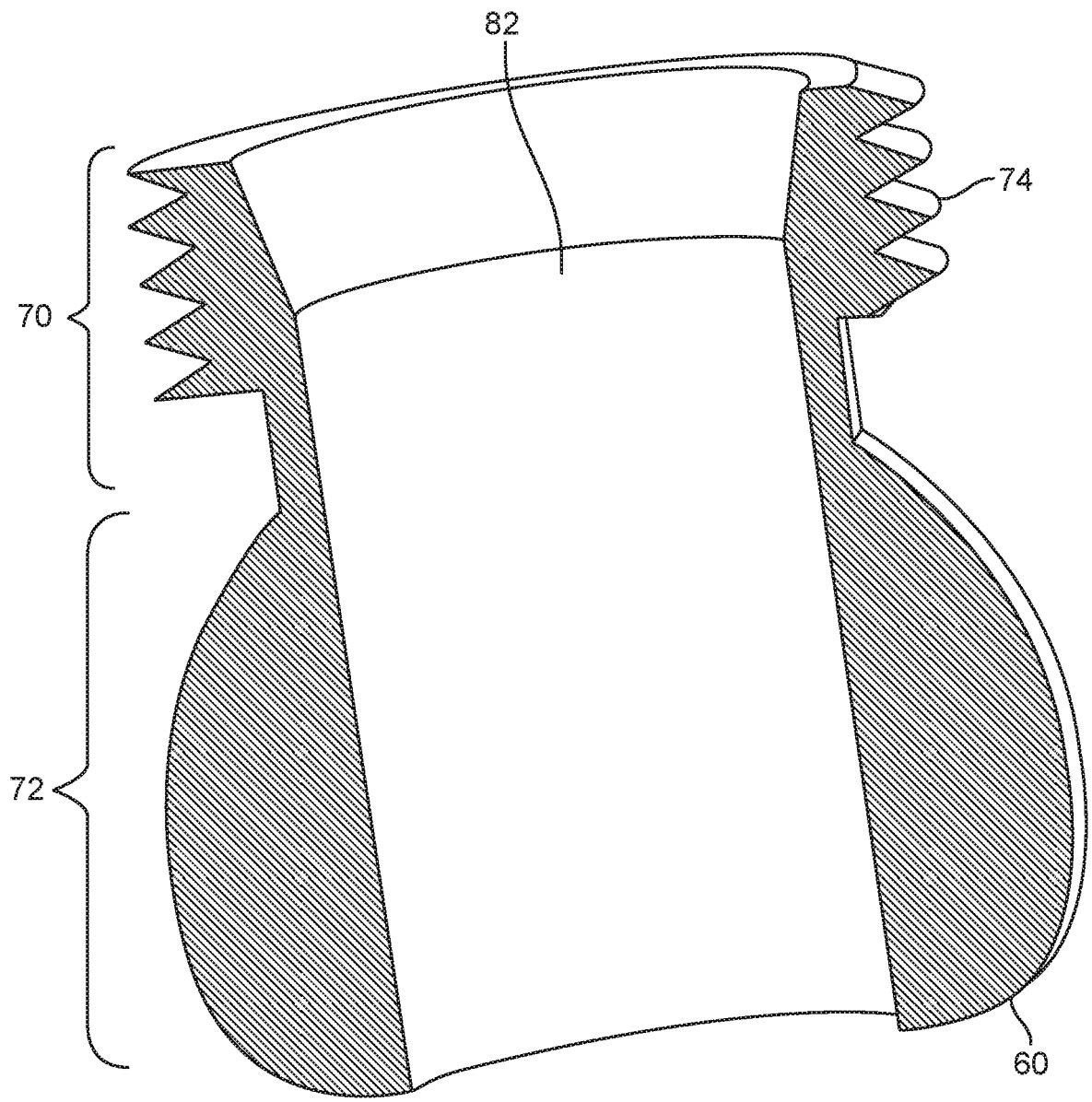
FIG. 14 is a cross sectional view of the component of FIG. 13.

Also viewed most easily in FIG. 12, ring 62 secures hub 66 to bulb 72. And bulb 72 is slidingly engaged to wand 52. Ring 62 has optional interlocking features 78 that receive or otherwise mate with threads 80. Other configurations such as engagement ribs or other suitable surface features designed to help secure ring 62 to hub 66 are within the scope of the invention. Wand 52 is disposed through a central aperture of each of the component parts of support assembly 54. Central aperture 82 of bulb 72 is most visible in FIG. 14. FIG. 14 is a cross sectional view of tilting element 60. Neck 70 and bulb 72 surround central aperture 82. When the desired angle of orientation of wand 52 is achieved, ring 62 is rotated clockwise to tighten engagement of hub 66 to bulb 72. When hub 66 is secured more tightly to bulb 72, (through a compression ring (not visible) or comparable structure), hub 72 can no longer be tilted about bulb 72. The angular orientation of wand 52 is thereby locked into place, leaving the position of wand 52 securely in place. The treating physician can then remove his or her hands from the system without compromising the optimal positioning of the system.

Figure 15:
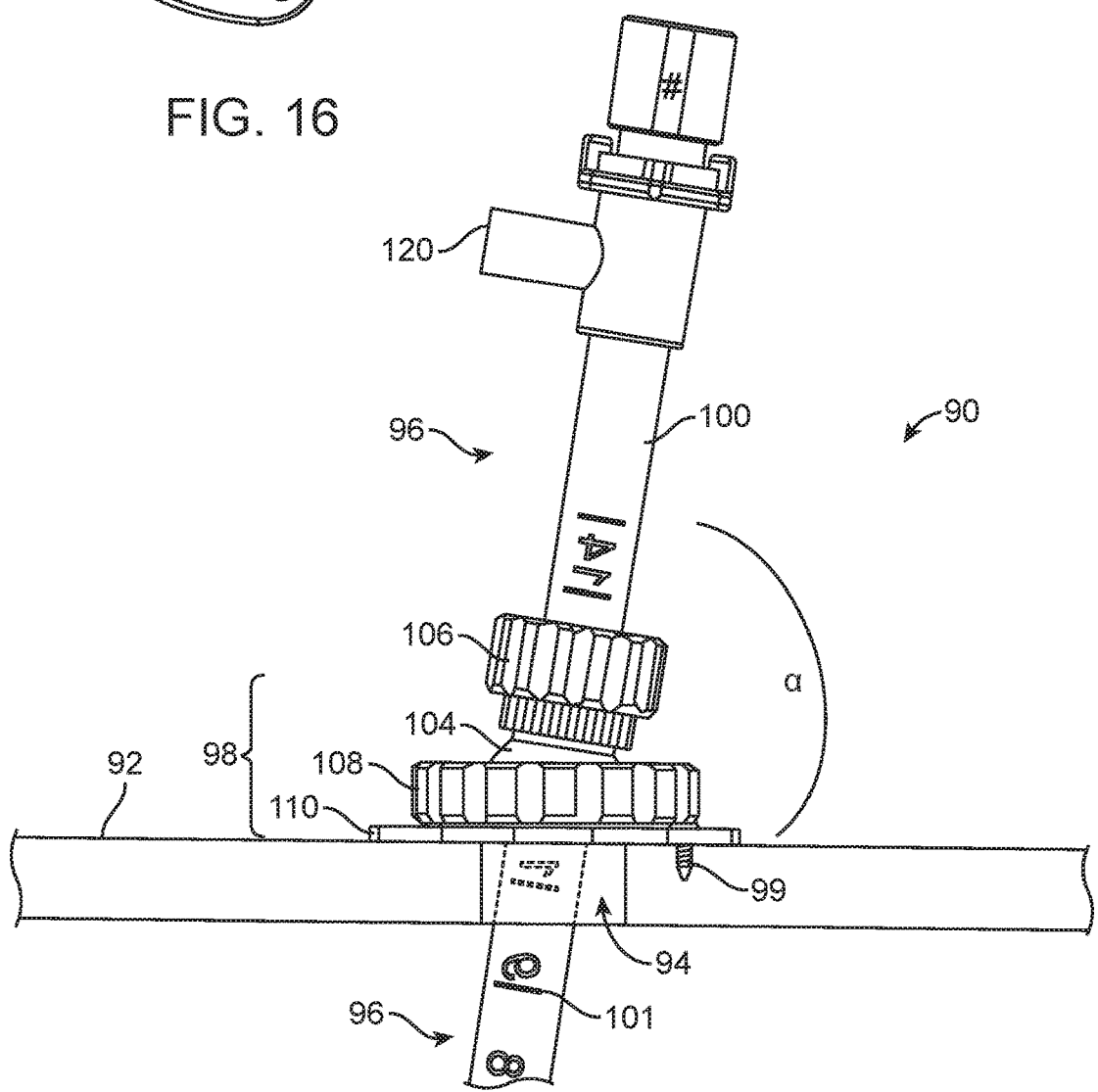
FIG. 15 is a side elevation view of an alternative embodiment according to the invention.

FIG. 15 illustrates an alternative embodiment according to the invention. The embodiment depicted in FIG. 15 includes many of the same components and capabilities of the embodiment illustrated in FIGS. 8-14, with some notable exceptions. Similar to the embodiments described above, the embodiment illustrated in FIG. 15 is configured to facilitate one or more intracranial medical procedures conducted through a burr hole in a skull of a subject.

Introducer 90 is illustrated in FIG. 15 in its working configuration. Introducer 90 is shown disposed with access to the interior of a patient's skull 92. Patient's skull 92 has been prepared by drilling burr hole 94, through which a portion of introducer 90 is disposed. Introducer 90 includes endoscope 96 and support assembly 98. Endoscope 96 can be seen disposed both above skull 92, and also within the interior of skull 92. Support assembly 98 is disposed primarily at the exterior of skull 92, with the exception of fastener 99, which is shown penetrating the bone of the skull, but not into the interior space of the skull 92.

Column 100 includes optional demarcations, or visual indicators 101. Column 100 is movable vertically through burr hole 94. The depth of introduction of column 100, or vertical positioning of column 100 is monitored via demarcations or visual indicators 101. In the side elevation view of introducer 90 featured in FIG. 15, column 100 is disposed at an angle α to skull 92. However, in use, the angle at which column 100 is disposed in relation to skull 92 is adjustable, at all points around its circumferential axis. Column 100 may be tilted vertically to the left of its position in FIG. 15, may be tilted towards the viewer of FIG. 15, or away from the viewer, and so on.

Support assembly 98 includes ball joint 104, collar 106, fitting 108, and adaptor plate 110. As mentioned above, column 100 is vertically movable. Further, collar 106 is configured to be either loosely engaged or tightened with respect to column 100. When collar 106 is tightened, column 100 is no longer movable vertically. In use, when a desired vertical position or depth of column 100 is achieved, the vertical position is secured via tightening of collar 106. Though not visible in FIG. 15, similar to embodiments described above, ball joint 104 may include a neck that is configured for adjustable, threaded engagement with the interior of collar 106. Collar 106 may otherwise be suitable configured for tighter or looser engagement with ball joint 104, and in turn, column 100.

Support assembly 98 is secured to skull 92 at burr hole 94 via adaptor plate 110. In the example of FIG. 15, adaptor plate 110 is secured to skull 92 via fastener 99. Fastener 99 is essentially a threaded bone screw, though it will be understood that other suitable means, such as for example staples, pins, tacks, sutures, adhesives, or other means, may be used for securing adaptor plate 110 to skull 92.

Though not visible in FIG. 15, similar to embodiments described above, the inside of fitting 108 may be in adjustable threaded engagement with a portion (not pictured) of adaptor plate 110. In the alternative, ball joint may be otherwise seated in the interior of fitting 108.

Introducer 90 is equipped with port 112. Port 112 is configured to accommodate tubing (not pictured) or a comparable structure or structures for delivering irrigation fluid to introducer 90. Port 112 may also be configured to accommodate an array of navigational features (not pictured) for enhanced visualization and/or manipulation of introducer, and for devices and instruments (not pictured) that are delivered to a treatment site via introducer 90. Optional navigation features may include stereotactic elements, wires, cables, or other components. Optional visualization features may include scopes, cameras, fiber optics, and other suitable elements. Whether navigational elements are used or not, introducer 90 is configured for introduction of any of a number of devices, through port 120 and/or through the top of column 100, in order to securely perform one or more intracranial medical procedures.

Figure 16:
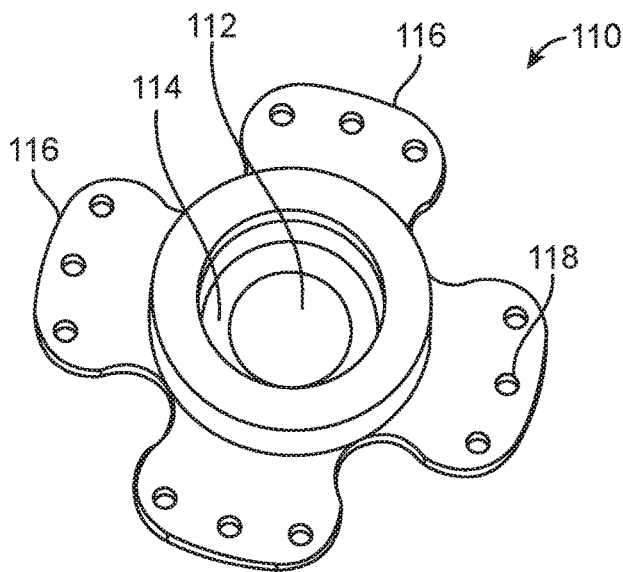
FIG. 16 is a perspective view of a first component of an alternative embodiment according to the invention.

FIG. 16 is a top perspective view of adaptor plate 110. Adaptor plate 110 includes central bore 112. Central bore 112 is sized and configured for positioning more or less concentrically with a burr hole of a patient's skull, and to accommodate ball joint 104, and the passage of column 100 therethrough. Hub 114 defines central bore 112. Further, arrayed about hub 114, generally about the periphery of central bore 112, are lobes 116. Lobes 116 are configured for supporting the other components of support assembly 98, and ultimately column 100. Lobes 116 are also configured for securing adaptor plate 110 to a patient's skull. In the example of FIGS. 15 and 16, lobes 116 include apertures 118. Screws (such as fastener 99 of FIG. 15) may be affixed to a patient's skull via apertures 118. In the alternative, staples, pins, adhesives, or other suitable fastening means may be used to secure adaptor plate 110 to a subject's skull.

Figure 17:
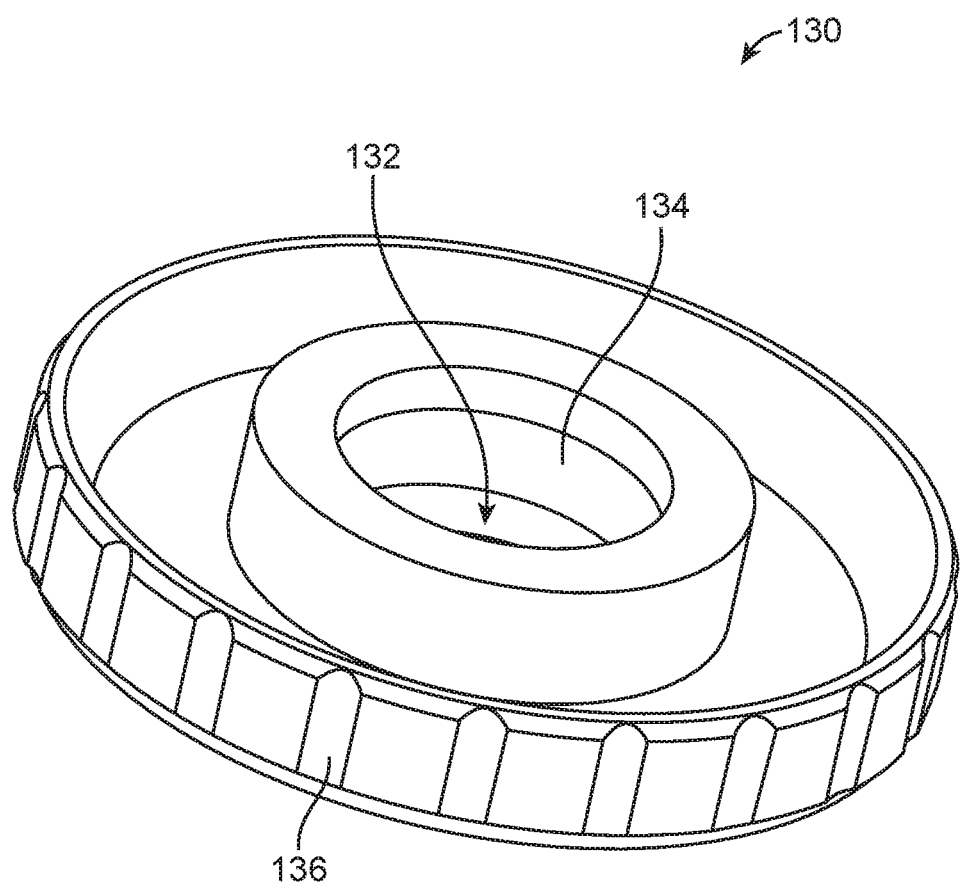
FIG. 17 is a top perspective view of a second component of an alternative embodiment according to the invention.
Figure 18:
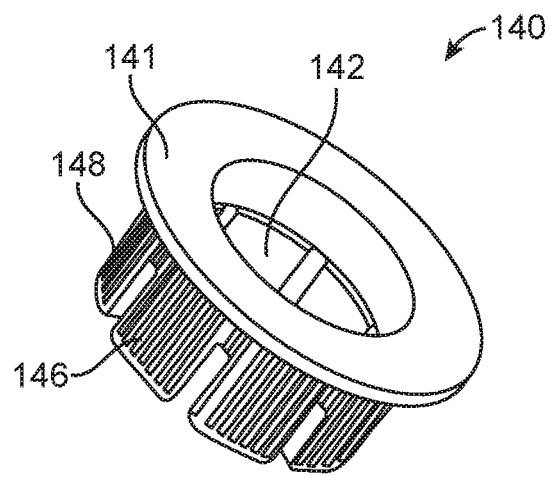
FIG. 18 is a top perspective view of a third component of an alternative embodiment according to the invention.
Figure 19:
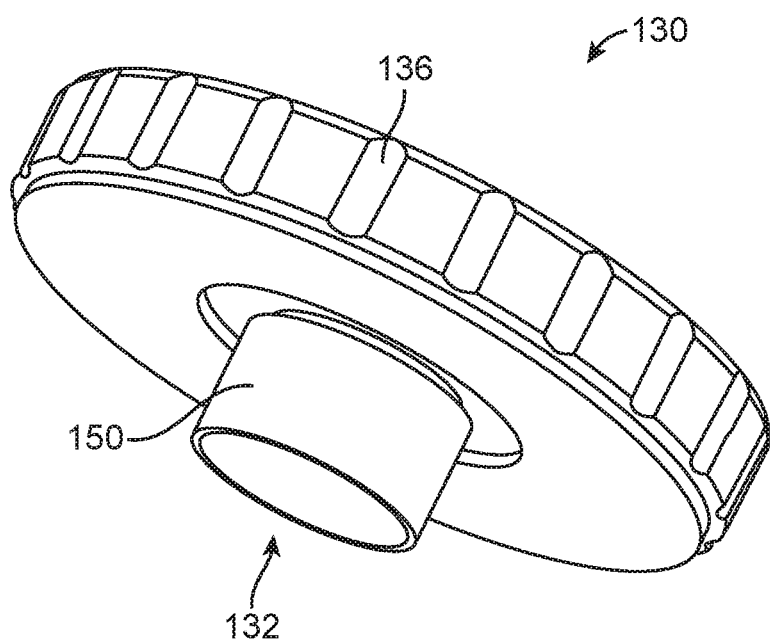
FIG. 19 is a bottom perspective view of the component of FIG. 17.

FIGS. 17-19 illustrate an alternative embodiment according to the invention. The components illustrated in FIGS. 17-19 may be used instead of adaptor plate 110 of FIGS. 15-16, or in addition to adaptor plate 110. In any event, the components illustrated in FIGS. 17-19 are configured to secure an introducer, such as, for example, introducer 90, when in use. FIG. 17 is a top perspective view of fitting 130. Fitting 130 includes a central bore 132, through which a ball joint of a support assembly, and a column of an introducer according to the invention can be disposed. Fitting 130 includes ball joint holder 134, in which a ball joint such as ball joint 104 may be disposed during use. Though not included in the example of FIG. 17, ball joint holder 134 may be equipped with threading, for threaded engagement with a ball joint sporting comparable features. Fitting 130 is equipped with grooves 136 for ergonomic handling. Additional features of fitting 130 are described below in conjunction with a description of FIG. 19.

FIG. 18 illustrates an alternative component for securing an introducer within a burr hole of a patient. FIG. 18 is a perspective view of socket 140. Socket 140 may be used in conjunction with any of the support assemblies described above. Socket 140 has a rim 141 and a central sleeve 142. Central sleeve 142 may include optional interior threads (not pictured). Central sleeve 142 also includes legs 146, and exterior ribs 148. Central sleeve 142 is in any event configured for secure placement within the burr hole of a patient (not pictured). In use, central sleeve 142 is placed within a burr hole of a subject (not pictured), with legs 146 securely seated against the interior of the burr hole. Rim 141 is seated around the top exterior of the burr hole.

Socket 140 works in conjunction with a fitting such as fitting 130 in order to securely accommodate an introducer in a burr hole of the skull of a patient. Socket 140 is first disposed within a burr hole of a patient as described above (not pictured), and then fitting 130 is disposed within socket 140. As illustrated in FIG. 19, stem 150 of fitting 130 is sized and configured for disposal within central sleeve 142 of socket 140. Stem 150 may be either threaded for secure engagement with the interior of central sleeve 142 (which may be complimentarily threaded), or may be sized for a friction fit with central sleeve 142, or, as an alternative, be manufactured from an expansible material for an enhanced, secure fit with socket 140. In any case, fitting 130 is secured by socket 140 within a burr hole of a patient, and is then ready to accommodate a ball joint or comparable structure such as illustrated in FIG. 15.

The foregoing examples are not intended to limit the scope of the invention. All modifications, equivalents and alternatives are within the scope of the invention. As an example, a proximal constraint element or a distal constraint element according to the invention need not be a sphere, but may be a disc, a block, a tear drop, or of any suitable alternative shape.

What is claimed is:

1. A system for use in performing an intracranial procedure on a subject, the system comprising:
    a column comprising at least one interior lumen, a transparent sheath, and an outer surface, wherein said outer surface includes symbols indicating depth in a mirror image orientation, whereby a visualization device passing through the interior lumen would be positioned to view the symbols indicating depth in a standard orientation;
    a ball joint disposed about said column;
    a support accessory disposed about said ball joint, said support accessory comprising a central aperture, a hub, and at least three lobes extending radially from said hub, said lobes configured to be secured to the skull of a subject; and
    a fitting disposed about said hub, whereby the column can be slidingly and tiltably engaged with the support assembly via the central aperture and the ball joint.

2. The system according to claim 1, wherein said column is configured for intracranial access to a subject via a burr hole placed in the skull of the subject.

3. The system according to claim 1, wherein said ball joint comprises a bulb, said hub comprises walls surrounding said central aperture, and said walls are configured to engage said bulb.

4. The system according to claim 1, wherein said lobes comprise a broadened segment.

5. The system according to claim 1, wherein said system further comprises a collar, and said ball joint further comprises a neck, wherein said neck engages said column, and said collar engages said neck, and said collar is configured for tightening and loosening engagement.

6. The system according to claim 5, wherein said collar and/or said neck comprise threading for adjustable engagement with one another.

7. The system according to claim 1, wherein said column comprises a port configured to accommodate one or more navigational elements.

8. The system according to claim 1, wherein said hub and said fitting are configured for threaded engagement with one another.

9. The system according to claim 1, wherein at least one of said lobes comprises one or more apertures for accommodating one or more fastening elements.

10. The system according to claim 1, wherein the system further comprises a socket configured for insertion into a burr hole of a subject, said socket also configured for receiving the support accessory therein.

11. The system according to claim 1, wherein the column includes an inner surface and the symbols indicating depth are in a standard orientation on the inner surface.

12. The system according to claim 11, wherein said sheath is configured to be peeled along a score line into two halves.

13. A system for use in performance of intracranial procedures via a burr hole in a skull of a subject, the system comprising:
    a column comprising at least one interior lumen;
    a ball joint disposed about said column;
    a support accessory disposed about said ball joint, said support accessory comprising a central aperture, a hub, and at least three lobes extending radially from said hub;
    a fitting comprised of an expandable stem and disposed about said hub; and
    a socket configured to be inserted into a burr hole of a subject, said socket configured to engage a burr hole and to engage said fitting, whereby the column can be slidingly and tiltably engaged with the support assembly via the central aperture and the ball joint.

14. The system according to claim 13, wherein said column is transparent and includes an outer surface, an inner surface, and symbols indicating depth that are in a mirror image orientation on the outer surface and are in a standard orientation on the inner surface.

15. The system according to claim 13, wherein said lobes comprise a broadened segment.

16. The system according to claim 13, wherein said system further comprises a collar, and said ball joint further comprises a neck, wherein said neck engages said column, and said collar engages said neck, and said collar is configured for tightening and loosening engagement.

17. The system according to claim 16, wherein said collar and/or said neck comprise threading for adjustable engagement with one another.

18. The system according to claim 13, wherein said column comprises a port configured to accommodate the introduction of irrigation fluids and/or one or more navigational elements.

19. The system according to claim 13, wherein said hub and said fitting are configured for threaded engagement with one another.

20. The system according to claim 13, wherein said column further comprises a sheath, and said sheath includes symbols indicating depth.

21. The system according to claim 20, wherein said sheath is configured to be separated into at least two pieces.

22. The system according to claim 13, wherein the socket is configured to receive the expandable stem in order to engage said fitting.

23. A support assembly for supporting an introducer for performing an intracranial medical procedure on a subject, the support assembly comprising:
    a ball joint configured to engage an introducer;
    a support accessory disposed about said ball joint, said support accessory comprising a central aperture, a hub, and at least three lobes extending radially from said hub, wherein at least one of said lobes comprises one or more apertures for accommodating one or more fastening elements; and a fitting comprised of an expandable stem and disposed about said hub;

whereby the introducer can be slidingly and tiltably engaged with the support assembly via the central aperture and the ball joint.

24. The assembly according to claim 23, wherein said assembly is configured for intracranial access to a subject via a burr hole placed in the skull of the subject.

25. The assembly according to claim 24, including a column with symbols indicating depth, wherein the column is configured for insertion into the burr hole.

26. The assembly according to claim 25, wherein the column is configured to be peeled along a score line into two halves.

27. The assembly according to claim 23, wherein said assembly further comprises a collar, and said ball joint further comprises a neck, wherein said neck is configured to engage an introducer, and said collar engages said neck, and said collar is configured for tightening and loosening engagement.

28. The assembly according to claim 27, wherein said collar and/or said neck comprise threading for adjustable engagement with one another.

29. The assembly according to claim 23, wherein said hub and said fitting are configured for threaded engagement with one another.

30. The assembly according to claim 23, wherein the assembly further comprises a socket configured for insertion into a burr hole of a subject, said socket also configured for receiving the support accessory therein.

31. A support assembly for supporting an introducer for performing an intracranial medical procedure on a subject via a burr hole in the skull of a subject, the support assembly comprising:

a column comprising at least one interior lumen, wherein the column is configured to be peeled along a score line into two halves;

a ball joint disposed about said column;

a support accessory disposed about said ball joint, said support accessory comprising a central aperture, a hub, and at least three lobes extending radially from said hub;

a fitting disposed about said hub; and a socket configured to be inserted into a burr hole of a subject, said socket configured to engage said fitting;

whereby the column can be slidingly and tiltably engaged with the support assembly via the central aperture and the ball joint.

32. The assembly according to claim 31, wherein the column includes symbols indicating depth.

33. The assembly according to claim 31, wherein the fitting includes an expandable stem.

34. The assembly according to claim 31, wherein said assembly further comprises a collar, and said ball joint further comprises a neck, wherein said neck is configured to engage an introducer, and said collar engages said neck, and said collar is configured for tightening and loosening engagement.

35. The assembly according to claim 34, wherein said collar and/or said neck comprise threading for adjustable engagement with one another.

36. The assembly according to claim 31, wherein said hub and said fitting are configured for threaded engagement with one another.

\* \* \* \* \*